United States Patent
Wang et al.

(10) Patent No.: US 9,517,262 B2
(45) Date of Patent: Dec. 13, 2016

(54) VACCINE INJECTION, PREPARATION METHOD AND USE THEREOF

(75) Inventors: Jiabo Wang, Beijing (CN); Xiaohe Xiao, Beijing (CN); Zhewei Wang, Beijing (CN); Cheng Jin, Beijing (CN); Qi Li, Beijing (CN)

(73) Assignees: CHINA 302 MILITARY HOSPITAL OF PLA, Beijing (CN); Jiabo Wang, Beijing (CN); Xiaohe Xiao, Beijing (CN); Zhewei Wang, Beijing (CN); Cheng Jin, Beijing (CN); Qi Li, Beijing (CN)

( * ) Notice: Subject to any disclaimer, the term of this patent is extended or adjusted under 35 U.S.C. 154(b) by 0 days.

(21) Appl. No.: 14/004,786

(22) PCT Filed: Apr. 8, 2011

(86) PCT No.: PCT/CN2011/072544
§ 371 (c)(1),
(2), (4) Date: Sep. 12, 2013

(87) PCT Pub. No.: WO2012/122725
PCT Pub. Date: Sep. 20, 2012

(65) Prior Publication Data
US 2014/0004150 A1 Jan. 2, 2014

(30) Foreign Application Priority Data

Mar. 16, 2011 (CN) .......................... 2011 1 0063283

(51) Int. Cl.
| | | |
|---|---|---|
| *A61K 39/00* | (2006.01) | |
| *A61K 39/39* | (2006.01) | |
| *A61K 39/29* | (2006.01) | |
| *A61K 39/07* | (2006.01) | |
| *A61K 39/08* | (2006.01) | |
| *A61K 39/02* | (2006.01) | |
| *A61K 39/112* | (2006.01) | |
| *A61K 39/145* | (2006.01) | |
| *A61K 39/165* | (2006.01) | |
| *A61K 39/20* | (2006.01) | |
| *A61K 39/05* | (2006.01) | |
| *A61K 39/12* | (2006.01) | |

(52) U.S. Cl.
CPC .............. *A61K 39/29* (2013.01); *A61K 39/00* (2013.01); *A61K 39/0208* (2013.01); *A61K 39/0275* (2013.01); *A61K 39/0291* (2013.01); *A61K 39/05* (2013.01); *A61K 39/07* (2013.01); *A61K 39/08* (2013.01); *A61K 39/098* (2013.01); *A61K 39/099* (2013.01); *A61K 39/12* (2013.01); *A61K 39/145* (2013.01); *A61K 39/165* (2013.01); *A61K 39/20* (2013.01); *A61K 39/39* (2013.01); *A61K 2039/54* (2013.01); *A61K 2039/55505* (2013.01); *A61K 2039/55588* (2013.01); *C12N 2760/18434* (2013.01); *C12N 2770/24134* (2013.01); *C12N 2770/32434* (2013.01)

(58) Field of Classification Search
None
See application file for complete search history.

(56) References Cited

FOREIGN PATENT DOCUMENTS

| | | |
|---|---|---|
| CN | 1367022 A | 9/2002 |
| EP | 1972347 A1 | 9/2008 |
| WO | WO0193829 A2 * | 12/2001 |

OTHER PUBLICATIONS

Skene et al. Saponin-adjuvanted particulate vaccines for clinical use. Methods. Sep. 2006;40(1):53-9.*
Tafaghodi et al. Preparation and in vivo study of dry powder microspheres for nasal immunization. J Drug Target. Apr. 2010;18(3):235-42.*
Sun et al. Immunologic enhancement of compound Chinese herbal medicinal ingredients and their efficacy comparison with compound Chinese herbal medicines. Vaccine. Mar. 20, 2006;24(13):2343-8. Epub Dec. 9. 2005.*
Maa et al. Stabilization of alum-adjuvanted vaccine dry powder formulations: mechanism and application. J Pharm Sci. Feb. 2003;92(2):319-32.*
Song et al. Adjuvant activities of saponins from traditional Chinese medicinal herbs. Vaccine 27 (2009) 4883-4890.*
Traditional Chinese Medicine: An Introduction. (http://nccam.nih.gov/health/whatiscam/chinesemed).*
http://en.wikipedia.org/wiki/Excipient.*
Tetanus toxoid for booster use only. http://www.fda.gov/downloads/BiologicsBloodVaccines/Vaccines/ApprovedProducts/UCM166873.pdf.*
Liang et al. Immunogenicity and safety of a novel formalin-inactivated and alum-adjuvanted candidate subunit vaccine for mumps. Vaccine. Aug. 5, 2008;26(33):4276-83. Epub Jun. 11, 2008.*
Sun et al. Engineering an Effective Immune Adjuvant by Designed Control of Shape and Crystallinity of Aluminum Oxyhydroxide Nanoparticles. ACS Nano. Dec. 23, 2013; 7(12): 10834-10849.*

(Continued)

*Primary Examiner* — Nick Zou
(74) *Attorney, Agent, or Firm* — Pearne & Gordon LLP

(57) ABSTRACT

The invention provides a vaccine injection, which includes a vaccine and a Traditional Chinese medicinal adjuvant in a mass ratio of 1:0.5-1:10, or a vaccine, a Traditional Chinese medicinal adjuvant and an aluminum adjuvant in a mass ratio of 1:0.5:2.5-1:10:20. The vaccine injection is in the form of powders, and the size of the powders is between 10 and 120 micrometers. The vaccine injection of the present invention is particularly suitable for the needle free injection technology. The invention also provides a preparation method for the vaccine injection.

8 Claims, No Drawings

(56) References Cited

OTHER PUBLICATIONS

E. Rivera et al. "Ginseng and aluminium hydroxide act synergistically as vaccine adjuvants" In: Vaccine, 2003, vol. 21, pp. 1149-1157.
International Search Report for PCT/CN2011/072544 Dec. 29, 2011.
Dexiang Chen et al. "Epidermal powder immunization of mice and monkeys with an influezna vaccine" In: Vaccine, 2003, vol. 21, pp. 2830-2836.
Xiuhua Lv et al. "The research status and development trend of the adjuvant of traditional Chinese medicine." In: CJTCMP, Jun. 2008, vol. 23, No. 6, pp. 517-530.

* cited by examiner

VACCINE INJECTION, PREPARATION METHOD AND USE THEREOF

TECHNICAL FIELD

The present invention relates to a vaccine injection, and the preparation method and use thereof, particularly to a vaccine injection in the form of powders, and the preparation method and use thereof.

BACKGROUND ART

Immunologic adjuvant refers to a substance which can non-specifically change or enhance the specific immune response of an organism to an antigen, and it is required to be non-cancerogenic, nontoxic, high-purity, degradable, of certain adsorbability and stable. The action principle of the immunologic adjuvant is mainly represented in the following three aspects: 1) increasing surface area of an antigen to improve the immunogenicity thereof; 2) playing slow-release function to the antigen to extend the retention time of the antigen in tissue; 3) promoting inflammatory reaction to stimulate active immune response. That is to say, the immunologic adjuvant causes the immune system to recognize the immunologic adjuvant itself also as an antigen, mainly by pseudomorphically pre-stimulating the immune system, and thus can cause a behavior of immune response of the organism more early. Currently, the common immunologic adjuvant comprises aluminium adjuvant, freund's adjuvant, CpG DNA adjuvant, nanoadjuvant, microorganism and the metabolite adjuvants thereof, and the like, wherein the activity of the freund's adjuvant is far higher than those of other types of adjuvants, however, the initiated side effect thereof is too intense, and thus cannot be widely used. Aluminium adjuvant is the only immunologic adjuvant currently approved to be used in human vaccine, which is used in various liquid vaccines. However, the aluminium adjuvant can only initiate humoral immunity, but cannot induce cell immunity, which increases limitation for its application. Moreover, the bonding capacity of the aluminium adjuvant with an antigen is not stable enough, and thus the potential toxic side effect of liquid aluminium element in vaccine after injecting in large dose also draws attention. Therefore, it has become an important task in the field of contemporary immunology research to find an efficient, secure, novel immunologic adjuvant.

Traditional Chinese medicine is an important part of the traditional medical theory of our country, which has its unique theoretical system and application form. Modern research shows that some of the active ingredients in the Traditional Chinese medicines (such as saponins, polysaccharides, flavonoids, etc.) possess good immunomodulatory effects. It is reported that: ginsenosides contained in ginseng, a traditional tonic Traditional Chinese medicine, can increase the activity of macrophages induce the generation of interferon, and stimulate the activity of cytotoxic T lymphocyte; *astragalus* polysaccharide can produce antagonism to some immunosuppressive drugs; icariin, as a main active ingredient of total flavonoids of herba epimedii, can increases the quality of immune organs, which makes the formation rate of E rosette and serum tumor necrosis factor-α level be significantly increased. Generally, the Traditional Chinese medicines are natural products, which have high bioaffinity, and the effects thereof are mild and persistent, therefore, their advantages, as novel vaccine adjuvants, are very significant, and thus they have drawn increasing attentions.

Currently, the vaccines containing adjuvants of Traditional Chinese medicines or Traditional Chinese medicinal ingredients have been developed and exploited to some extent. However, the vaccine itself which contains an adjuvant of Traditional Chinese medicine or Traditional Chinese medicinal ingredient has problems of non-ideal effect and inconvenient use. Therefore, there is a need for an efficient, convenient vaccine injection.

CONTENT OF THE INVENTION

The primary object of the present invention is to provide a vaccine injection.

Another object of the present invention is to provide a method for preparing the vaccine injection.

Another object of the present invention is to provide use of the vaccine injection in the preparation of a medicament for preventing or treating diseases.

Still another object of the present invention is to provide a method for needle free injection by using the vaccine injection.

In a first aspect, the vaccine injection of the present invention comprises a vaccine and a Traditional Chinese medicinal adjuvant in a mass ratio of 1:0.5-1:10. The vaccine injection is a form of powders and the particle size of the powders is between 10-120 micrometers. Preferably, the mass ratio is 1:1-1:5, and the particle size of the powders is between 30-70 micrometers.

In an embodiment of the first aspect, said vaccine is selected from tetanus toxoid vaccine, mumps vaccine, diphtheria vaccine, pertussis vaccine, measles vaccine, rubella vaccine, typhoid vaccine, b-type influenza vaccine, plague vaccine, anthrax vaccine, Brucella vaccine, leptospira vaccine, Japanese encephalitis vaccine, hepatitis A vaccine and forest encephalitis vaccine.

In an embodiment of the first aspect, the Traditional Chinese medicinal adjuvant is selected from saponins, polysaccharides and flavonoid.

Preferably, the saponins are selected from ginsenoside, notoginsenoside, gypenoside, Clematis saponin and dioscin, etc.; the polysaccharides are selected from *astragalus* polysaccharide, ginseng polysaccharide, grifola polysaccharide, Rhodiola polysaccharide and jujube polysaccharide; the flavonoids are selected from epimedium flavonoid, kumquat flavonoid, *Hedyotis diffusa* flavonoid, daidzein and sea buckthorn flavonoid, and the like.

In an embodiment of the first aspect, the vaccine injection is prepared by directly mixing and then freeze-drying.

In an embodiment of the first aspect, the vaccine injection is administered by needle free injection. In a second aspect, the vaccine injection of the present invention comprises a vaccine, a Traditional Chinese medicinal adjuvant and an aluminum adjuvant in a mass ratio of 1:0.5:2.5-1:10:20. The vaccine injection is in the form of powders and the particle size of the powders is between 10-120 micrometers. Preferably, the mass ratio is 1:1:5-1:1:10, and the particle size of the powders is between 30-70 micrometers.

In an embodiment of the second aspect, said vaccine is selected from tetanus toxoid vaccine, mumps vaccine, diphtheria vaccine, pertussis vaccine, measles vaccine, rubella vaccine, typhoid vaccine, b-type influenza vaccine, plague vaccine, anthrax vaccine, Brucella vaccine, leptospira vaccine, Japanese encephalitis vaccine, hepatitis A vaccine and forest encephalitis vaccine.

In an embodiment of the second aspect, the Traditional Chinese medicinal adjuvant is selected from saponins, polysaccharides and flavonoids.

Preferably, the saponin is selected from ginsenoside, notoginsenoside, gypenoside, Clematis saponin and dioscin, etc.; the polysaccharide is selected from *astragalus* polysaccharide, ginseng polysaccharide, grifola polysaccharide, Rhodiola polysaccharide and jujube polysaccharide; the flavonoid is selected from epimedium flavonoid, kumquat flavonoid, *Hedyotis diffusa* flavonoid, daidzein and sea buckthorn flavonoid, and the like.

In an embodiment of the second aspect, a solution of the vaccine injection is prepared by a dispersion-adsorption method or aluminum column adsorption method.

In an embodiment of the second aspect, the vaccine injection is administered by needle free injection.

In a third aspect, the present invention provides a method for preparing the vaccine injection of the present invention.

In one embodiment, the method for preparing the vaccine injection of the present invention comprises the following steps: sufficiently mixing a vaccine and a Traditional Chinese medicinal adjuvant in a mass ratio of 1:0.5-1:10 in a liquid environment; after drying, collecting powders with particle sizes between 10-120 micrometers to obtain the vaccine injection of the present invention. Preferably, the mass ratio is 1:1-1:5, and the particle size is between 30-70 micrometers.

Preferably, the method for preparing the vaccine injection of the present invention comprises the following steps:

① sodium chloride is weighed, and is prepared with double distilled water to form a sodium chloride solution with a concentration of 1 mol/l, and then moist heat sterilization is carried out;

② an appropriate amount of the required Traditional Chinese medicinal ingredient adjuvant is weighed, and is prepared with double distilled water to form a solution of Traditional Chinese medicinal ingredient adjuvant with a concentration of 0.5-5 mg/ml, and moist heat sterilization is carried out;

③ appropriate amounts of vaccine solution and solution of Traditional Chinese medicinal ingredient adjuvant prepared in step ② are added into the sodium chloride solution prepared in step ① in a mass ratio of the vaccine to the Traditional Chinese medicinal adjuvant of 1:0.5-1:10, mixed uniformly such that the volume of the final solution is 5 ml, the concentration of the vaccine is 200-800 μg/ml, the concentration of the Traditional Chinese medicinal adjuvant is 50-2000 μg/ml, and the concentration of the sodium chloride is 0.4 mol/l, and then the resulted mixture is allowed to stand for 15 minutes at room temperature to obtain a mixed suspension;

④ the mixed suspension prepared in step ③ is centrifuged at 2000-4000 times of gravitational acceleration for 20-30 minutes, the supernatant is discarded and the precipitate is freeze-dried, the powders with particle sizes between 20-80 micrometers are collected to obtain the vaccine injection of the present invention.

In another embodiment, the method for preparing the vaccine injection of the present invention comprises the following steps: in a liquid environment, adsorbing a vaccine onto an aluminium adjuvant in an amount such that the mass ratio of the vaccine to the aluminium adjuvant is 1:2.5-1:20, after drying, collecting the powders with particle sizes between 10-120 micrometers, and then adding the powders of a Traditional Chinese medicinal adjuvant with particle sizes between 10-120 micrometers in an amount such that the mass ratio of the vaccine, the Traditional Chinese medicinal adjuvant and the aluminium adjuvant is 1:0.5:2.5-1:10:20, mixing uniformly to obtain the vaccine injection of the present invention. Preferably, the mass ratio is 1:1:5-1:1:10, and the particle size is between 30-70 micrometers.

Preferably, the method for preparing the vaccine injection of the present invention comprises the following steps:

① aluminum sulfate or aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for about 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 70-130 mg of the above aluminum hydroxide adsorbed powders are resuspended in 2-8 ml double distilled water, and is subjected to ultrasonic processing, dispersed for 2 hours, and subjected to moist heat sterilization to give a suspension of aluminum hydroxide in water;

⑥ sodium chloride is weighed, and is prepared with double distilled water to form a sodium chloride solution with a concentration of 1 mol/l, and then subjected to moist heat sterilization;

⑦ to 0.5 ml of the suspension of aluminum hydroxide in water obtained in step ⑤, appropriate amounts of a vaccine solution and the sodium chloride solution obtained in step ⑥ are added, mixed uniformly such that the volume of the final solution is 5 ml, the concentration of vaccine is 200-800 μg/ml, and the concentration of sodium chloride is 0.4 mol/l, and a mixed suspension is obtained upon standing for 15 minutes at room temperature;

⑧ the mixed suspension prepared in step ⑦ is centrifuged at 2000-4000 times of gravitational acceleration for 20-30 minutes, the supernatant is discarded and the precipitate is freeze-dried, the powders with particle sizes between about 30-70 micrometers are collected to obtain drug-loaded aluminium hydroxide powders;

⑨ an appropriate amount of the powders of the Traditional Chinese medicinal adjuvant is weighed, the powders with particle sizes between 30-70 micrometers are collected, the powders of the Traditional Chinese medicinal adjuvant are uniformly mixed with the above drug-loaded aluminium hydroxide powders in a mass ratio of the vaccine:the Traditional Chinese medicinal adjuvant of 1:0.5-1:10 to obtain the vaccine injection of the present invention.

In another embodiment, the method for preparing the vaccine injection of the present invention comprises: in a liquid environment, the vaccine is mixed together with an aluminium adjuvant and Traditional Chinese medicine powders in a mass ratio of 1:0.5:2.5-1:10:20 of the vaccine, the aluminium adjuvant and the Traditional Chinese medicine powders for adsorption, after drying and uniformly mixing, the powders with particle sizes between 10-120 micrometers are collected to obtain the vaccine injection of the present invention. Preferably, the mass ratio is 1:1:5-1:1:10, and the particle size is between 30-70 micrometers.

Preferably, the method for preparing the vaccine injection of the present invention comprises the following steps:

① aluminum sulfate or aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for about 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ about 100 mg of the above aluminum hydroxide adsorbed powders are resuspended in 2-8 ml double distilled water, and then subjected to ultrasonic processing, dispersed for 2 hours, and subjected to moist heat sterilization to give a mixed suspension;

⑥ an appropriate amount of the required Traditional Chinese medicinal ingredient adjuvant is weighed, and is prepared with double distilled water to form a solution of the Traditional Chinese medicinal ingredient adjuvant with a concentration of 0.1-1 mg/ml, and then subjected to moist heat sterilization;

⑦ sodium chloride is weighed, and is prepared with double distilled water to form a sodium chloride solution with a concentration of 0.5-2 mol/l, and subjected to moist heat sterilization;

⑧ to 0.5 ml of the mixed suspension obtained in step ⑤, the solution of the Traditional Chinese medicinal ingredient adjuvant obtained in step ⑥ is added in a mass ratio of the vaccine to the Traditional Chinese medicinal adjuvant of 1:0.5-1:10, and then appropriate amounts of a vaccine solution and the sodium chloride solution obtained in step ⑦ is added, mixed uniformly so that the volume of the final solution is 5 ml, the concentration of vaccine is 200-800 μg/ml, and the concentration of sodium chloride is 0.4 mol/l, and a mixed suspension is obtained upon standing for 15 minutes at room temperature;

⑨ the mixed suspension is centrifuged at 2000-4000 times of gravitational acceleration for 20-30 minutes, and the supernatant is discarded;

⑩ the above obtained precipitate is freeze-dried, the powders with particle sizes between about 30-70 micrometers are collected to obtain the vaccine injection.

In yet another embodiment, the method for preparing the vaccine injection of the present invention comprises: preparing an aluminum adsorption column with aluminum hydroxide as a supporter, a vaccine solution and a solution of a Traditional Chinese medicinal adjuvant flowing through the aluminum adsorption column, drying the aluminum adsorption column, collecting powders with particle sizes between 10-120 micrometers to obtain the vaccine injection of the present invention. Preferably, the particle size is between 30-70 micrometers.

Preferably, the step of the vaccine solution and the solution of the Traditional Chinese medicinal adjuvant flowing through the aluminum adsorption column comprises: the vaccine solution flowing through the aluminum adsorption column, and then the solution of the Traditional Chinese medicinal adjuvant flowing through the aluminum adsorption column; or, the solution of the Traditional Chinese medicinal adjuvant flowing through the aluminum adsorption column, and then the vaccine solution flowing through the aluminum adsorption column; or, mixing the vaccine solution and the solution of the Traditional Chinese medicinal adjuvant together, and then the mixed solution flowing through the aluminum adsorption column.

Preferably, the method for preparing the vaccine injection of the present invention comprises the following steps:

① aluminum sulfate or aluminum nitrate is added into double distilled water and dissolved to prepare a saturated solution, and the insolubles are filtered off;

② an aqueous ammonia is added dropwisely into the above saturated solution with stirring slowly until the generated white flocculent precipitate does not increase any more, and then allowed to stand for about 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 0.5-2 g of the aluminum hydroxide powders obtained in step ④ are weighed, loaded into a cylindrical tube with a diameter of 0.3-3 cm and a length of 4-15 cm, a filter membrane with pore sizes of 10-30 micrometers is installed at the outlet at the bottom of the tube to make a aluminum adsorption column;

⑥ the required Traditional Chinese medicinal ingredient adjuvant is weighed in a ratio such that the final mass of the vaccine:the final mass of the Traditional Chinese medicinal adjuvant is 1:0.5-1:10, and then the required Traditional Chinese medicinal ingredient adjuvant is prepared with double distilled water to form a solution of the Traditional Chinese medicinal ingredient adjuvant with a concentration of 0.1-1 mg/ml, and subjected to moist heat sterilization;

⑦ the aluminum adsorption column is placed vertically, the vaccine solution flows slowly through the aluminum adsorption column from top to bottom at a certain rate, the outlet of the tube is closed when the aluminum adsorption column is sufficiently immersed by the vaccine solution, the outlet is opened after equilibrium adsorption for 10-30 minutes to allow the vaccine solution to flow out, and then the solution of the Traditional Chinese medicinal ingredient adjuvant flows into the aluminum adsorption column in the same way for adsorption; or, firstly, the solution of Traditional Chinese medicinal ingredient adjuvant flows into the aluminum adsorption column, and then the vaccine solution is allowed to flow into the aluminum adsorption column in the same way for adsorption; or, the vaccine solution and the solution of the Traditional Chinese medicinal ingredient adjuvant are mixed together and then flow into the aluminum column for adsorption;

⑧ the adsorbed aluminum column is decant from the tube after freeze-drying, the powders with particle sizes between 20-80 micrometers are collected to obtain the vaccine injection of the present invention.

The vaccine injection of the present invention can be used to prepare a medicament for preventing or treating a variety of diseases. These diseases include, but are not limited to, pertussis, tetanus, mumps, diphtheria, measles, rubella, typhoid, b-type influenza, brucellosis, leptospirosis, Japanese encephalitis, hepatitis A, anthrax, plague, forest encephalitis.

When used, the prepared vaccine injection is fitted with a needle free injector. The vaccine injection loaded in a kit is transmitted into the histiocyte of skin and releases a drug subcutaneously or in mucosal tissue by the needle free injector with a gas storage device, a force generating device, and a launching device. In general, the vaccine injection is loaded into the kit of the needle free injector. Preferably, 10-75 μg of the vaccine injection is loaded into the kit of the needle free injector.

The vaccine injection of the present invention has both the advantages of aluminium adjuvant and Traditional Chinese medicinal adjuvant. Aluminum hydroxide particles as an aluminium adjuvant have a high surface energy, and are capable of generating adsorption for substances such as a protein, so that the vaccine is combined to the surface of the aluminum hydroxide particles and they finally form a stable powder system together. Moreover, aluminum hydroxide itself, in addition to acting as an immunologic adjuvant, also possesses flocculent adsorption function, and a substrate of solid vaccine developed on the basis of the adsorption function can give full play to the pharmaceutic advantage thereof. The Traditional Chinese medicinal adjuvant has certain absorption and loading ability, which can assist in solidification, and thus makes up for the lack of absorption capacity of the aluminum adjuvant. Furthermore, the immune response caused by a Traditional Chinese medicinal adjuvant is more complex, which can induce both humoral immunity and cell immunity. On the other hand, since the Traditional Chinese medicinal adjuvant reaching the administration site is solid powder microparticles, and the microparticles themselves are intensely immunogenic, the pre-stimulation generated on immune system is more intense; at the same time, since the diffusion rate of the solid formulation via the body fluid in vivo is low, and it is not easy for the aluminium element in a composite adjuvant to enter into the fluid circulation, the vaccine injection not only reduces the side effect of the aluminum adjuvant, but also has some slow-release effect.

The vaccine injection of the present invention provides a new formulation of vaccine, which is especially suitable for needle free injection technology, and thus effectively avoids the first pass effect due to oral pharmaceutical preparation. The particle size of the vaccine injection is in conformity with the requirement for percutaneous administration, easy to pass the stratum corneum barrier, and can significantly improve drug efficacy and shorten the onset time. Therefore, the vaccine injection adapted for needle free injection technology is especially suitable for medical prevention guarantee in the condition of serious emergencies and remote areas, large-scale field operations and the like, and a patient who fears needle (e.g., children) and a patient who requires long-term self-administration. Such a formulation is more stable, and thus has a very broad application prospect.

The present invention adopts solution dispersion-adsorption and aluminum adsorption column methods to prepare a powder injection vaccine. The process of the solution dispersion-adsorption method is convenient, the procedure is short, and the cost is low; while the aluminum adsorption column method is suitable for the preparation of powders in large-scale.

PREFERRED EMBODIMENT OF THE INVENTION

The substances used in the following Examples, unless specified, are all commercially available.

Example 1

A notoginsenoside-containing pertussis vaccine injection is prepared in a manner of directly mixing solutions:

① sodium chloride is weighed, and is prepared with double distilled water to form a sodium chloride solution with a concentration of 1 mol/l, and then moist heat sterilization is carried out;

② 6 g notoginsenoside is weighed, and is prepared with double distilled water to form a notoginsenoside solution with a concentration of 1.2 mg/ml, and moist heat sterilization is carried out;

③ a pertussis vaccine solution and the solution of notoginsenoside prepared in step ② are added to the sodium chloride solution prepared in step ① in a mass ratio of the pertussis vaccine:the mass of notoginsenoside of 1:6, mixed uniformly such that the volume of the final solution is 5 ml, the concentration of pertussis vaccine is 100 μg/ml, the concentration of notoginsenoside is 600 μg/ml, and the concentration of sodium chloride is 0.4 mol/l, and a mixed suspension is obtained upon standing for 15 minutes at room temperature;

④ the mixed suspension prepared in step ③ is centrifuged at 2400 times of gravitational acceleration for 30 minutes, the supernatant is discarded and the precipitate is freeze-dried, the powders with particle sizes between about 20-80 micrometers are collected to obtain the notoginsenoside-containing pertussis vaccine injection.

Example 2

A ginsenoside-containing tetanus toxoid vaccine injection is prepared by solution dispersion-adsorption method in a manner of solidly mixing the Traditional Chinese medicinal adjuvant:

① 15 g aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 100 mg of the above aluminum hydroxide adsorbed powders are resuspended in 7 ml double distilled water, and then subjected to ultrasonic processing in a ultrasonic cleaner, dispersed for 2 hours, and subjected to moist heat sterilization to give a suspension of aluminum hydroxide in water;

⑥ sodium chloride is weighed, and is prepared with double distilled water to form a sodium chloride solution with a concentration of 1 mol/l, and then moist heat sterilization is carried out;

⑦ to 0.5 ml of the suspension of aluminum hydroxide in water obtained in step ⑤, a tetanus toxoid vaccine solution and the sodium chloride solution obtained in step ⑥ are added, mixed uniformly such that the volume of the final solution is 5 ml, the concentration of tetanus toxoid vaccine is 500 μg/ml, and the concentration of sodium chloride is 0.4 mol/l, and a mixed suspension is obtained upon standing for 15 minutes at room temperature;

⑧ the mixed suspension in step ⑦ is centrifuged at 3500 times of gravitational acceleration for 30 minutes, the supernatant is discarded and the precipitate is freeze-dried, the powders with particle sizes between about 30-70 micrometers are collected to obtain drug-loaded aluminium hydroxide powders of tetanus toxoid vaccine;

⑨ 5 g ginsenoside is weighed, the ginsenoside powders with particle sizes equivalent to those of drug-loaded aluminium hydroxide powders of tetanus toxoid vaccine, i.e. between about 30-70 micrometers, are collected, mixed uniformly with the above drug-loaded aluminium hydroxide powders of tetanus toxoid vaccine in a mass ratio of the vaccine:the Traditional Chinese medicinal adjuvant of 1:1, to obtain the ginsenoside-containing tetanus toxoid vaccine injection.

Example 3

An *astragalus* polysaccharide-containing mumps vaccine injection is prepared by solution dispersion-adsorption method in a manner of liquidly mixing the Traditional Chinese medicinal adjuvant:

① 15 g aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 100 mg of the above aluminum hydroxide adsorbed powders are resuspended in 7 ml double distilled water, and then subjected to ultrasonic processing in a ultrasonic cleaner, dispersed for 2 hours, and subjected to moist heat sterilization to give a suspension of aluminum hydroxide in water;

⑥ 5 g *astragalus* polysaccharides is weighed, and is prepared with double distilled water to form an *astragalus* polysaccharide solution with a concentration of 0.5 mg/ml, and then moist heat sterilization is carried out;

⑦ sodium chloride is weighed, and is prepared with double distilled water to form a sodium chloride solution with a concentration of 1 mol/l, and then moist heat sterilization is performed;

⑧ to 0.5 ml suspension of aluminum hydroxide in water obtained in step ⑤, a mumps vaccine solution and the *astragalus* polysaccharide solution obtained in step ⑥ are added in a mass ratio of the vaccine:the Traditional Chinese medicinal adjuvant of 1:1, and the sodium chloride solution obtained in step ⑦ is added, mixed uniformly such that the volume of the final solution is 5 ml, the concentration of mumps vaccine is 500 μg/ml, and the concentration of sodium chloride is 0.4 mol/l, and a mixed suspension is obtained upon standing for 15 minutes at room temperature;

⑨ the mixed suspension obtained in step ⑧ is centrifuged at 3500 times of gravitational acceleration for 30 minutes, and the supernatant is discarded;

⑩ the precipitate obtained in step ⑨ is freeze-dried, the powders with particle sizes between about 30-70 micrometers are collected to obtain the *astragalus* polysaccharide-containing mumps vaccine injection.

Example 4

An epimedium flavonoid-containing diphtheria vaccine injection is prepared by an aluminum column adsorption method:

① 15 g aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 1 g of the aluminum hydroxide powders obtained in step ④ is weighed, loaded into a cylindrical tube with a diameter of 1 cm and a length of 10 cm, and a filter membrane with a pore size of 22 micrometer is installed at the outlet at the bottom of the tube to make an aluminum adsorption column;

⑥ 1.5 g epimedium flavonoid is weighed, and the amount of diphtheria vaccine solution is determined according to a mass ratio of the final vaccine:the final Traditional Chinese medicinal adjuvant of 1:2, the epimedium flavonoid is prepared with double distilled water to form a solution with a concentration of 0.3 mg/ml, and then moist heat sterilization is carried out;

⑦ the aluminum adsorption column is placed vertically, the diphtheria vaccine solution flows slowly through the aluminum adsorption column from top to bottom at a rate of 0.2 ml/min, the outlet of the tube is closed when the aluminum adsorption column is sufficiently immersed by the vaccine solution, the outlet is opened after equilibrium adsorption for 25 minutes to allow the vaccine solution to flow out, and then the epimedium flavonoid solution flows through the aluminum column in the same way for adsorption;

⑧ the adsorbed aluminum column is decant from the tube after freeze-drying, the powders with particle sizes between about 40-60 micrometers are collected to obtain the epimedium flavonoid-containing diphtheria vaccine injection.

Example 5

A grifola polysaccharide-containing measles vaccine injection is prepared in a manner of directly mixing the solutions:

① sodium chloride is weighed, and is prepared with double distilled water to form a sodium chloride solution with a concentration of 1 mol/l, and moist heat sterilization is carried out;

② 5.5 g grifola polysaccharide is weighed, and is prepared with double distilled water to form a grifola polysaccharide solution with a concentration of 1.1 mg/ml, and moist heat sterilization is carried out;

③ a measles vaccine solution and the grifola polysaccharide solution prepared in step ② are added to the sodium chloride solution prepared in step ① in a mass ratio of the measles vaccine:the grifola polysaccharide of 1:8, mixed uniformly such that the volume of the final solution is 5 ml, the concentration of measles vaccine is 50 μg/ml, the concentration of grifola polysaccharide is 400 μg/ml, and the concentration of sodium chloride is 0.4 mol/l, and a mixed suspension is obtained upon standing for 15 minutes at room temperature;

④ the mixed suspension prepared in step ③ is centrifuged at 3000 times of gravitational acceleration for 30 minutes, the supernatant is discarded and the precipitate is freeze-dried, the powders with particle sizes between about 20-80 micrometers are collected to obtain the grifola polysaccharide-containing measles vaccine injection.

Example 6

A *Hedyotis diffusa* flavonoid-containing rubella vaccine injection is prepared by a solution dispersion-adsorption method in a manner of solidly mixing the Traditional Chinese medicinal adjuvant:

① 24 g aluminum sulfate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 100 mg of the above aluminum hydroxide adsorbed powders are resuspended in 8 ml double distilled water, and then subjected to ultrasonic processing in a ultrasonic cleaner, dispersed for 2 hours, and subjected to moist heat sterilization to give a suspension of aluminum hydroxide in water;

⑥ sodium chloride is weighed, and is prepared with double distilled water into form a sodium chloride solution with a concentration of 1 mol/l, and then moist heat sterilization is carried out;

⑦ to 0.5 ml of the suspension of aluminum hydroxide in water obtained in step ⑤, a rubella vaccine solution and the sodium chloride solution obtained in step ⑥ are added, mixed uniformly such that the volume of the final solution is 5 ml, the concentration of rubella vaccine is 550 μg/ml, and the concentration of sodium chloride is 0.4 mol/l, and a mixed suspension is obtained upon standing for 15 minutes at room temperature;

⑧ the mixed suspension in step ⑦ is centrifuged at 3200 times of gravitational acceleration for 30 minutes, the supernatant is discarded and the precipitate is freeze-dried, the powders with particle sizes between about 30-70 micrometers are collected to obtain drug-loaded aluminium hydroxide powders of rubella vaccine;

⑨ 4 g *Hedyotis diffusa* flavonoid is weighed, the *Hedyotis diffusa* flavonoid powders with particle sizes equivalent to those of the drug-loaded aluminium hydroxide powders of rubella vaccine, i.e. between about 30-70 micrometers, are collected, mixed uniformly with the above drug-loaded aluminium hydroxide powders of rubella vaccine in a mass ratio of the vaccine:the Traditional Chinese medicinal adjuvant of 1:1.2, to obtain the *Hedyotis diffusa* flavonoid-containing rubella vaccine injection.

Example 7

A jujube polysaccharide-containing typhoid vaccine injection is prepared by a solution dispersion-adsorption method in a manner of liquidly mixing the Traditional Chinese medicinal adjuvant:

① 22 g aluminum sulfate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 100 mg of the above aluminum hydroxide adsorbed powders are resuspended in 7 ml double distilled water, and then subjected to ultrasonic processing in a ultrasonic cleaner, dispersed for 2 hours, and subjected to moist heat sterilization to give a suspension of aluminum hydroxide in water;

⑥ 4.5 g jujube polysaccharide is weighed, and is prepared with double distilled water to form a jujube polysaccharide solution with a concentration of 0.5 mg/ml, and then moist heat sterilization is carried out;

⑦ sodium chloride is weighed, and is prepared with double distilled water to form a sodium chloride solution with a concentration of 1 mol/l, and then moist heat sterilization is carried out;

⑧ to 0.5 ml of the suspension of aluminum hydroxide in water obtained in step ⑤, a typhoid vaccine solution and the jujube polysaccharide solution obtained in step ⑥ are added in a mass ratio of the vaccine:the Traditional Chinese medicinal adjuvant of 1:1, and the sodium chloride solution obtained in step ⑦ is added, mixed uniformly such that the volume of the final solution is 5 ml, the concentration of the typhoid vaccine is 500 μg/ml, and the concentration of sodium chloride is 0.4 mol/l, and a mixed suspension is obtained upon standing for 15 minutes at room temperature;

⑨ the mixed suspension in step ⑧ is centrifuged at 3500 times of gravitational acceleration for 30 minutes, and the supernatant is discarded;

⑩ the precipitate obtained in step ⑨ is freeze-dried, and the powders with particle sizes between about 30-70 micrometers are collected to obtain the jujube polysaccharide-containing typhoid vaccine injection.

Example 8

A gypenoside-containing b-type influenza vaccine injection is prepared by an aluminum column adsorption method:

① 16 g aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 1.5 g of the aluminum hydroxide powders obtained in step ④ is weighed, and loaded into a cylindrical tube with a diameter of 1 cm and a length of 10 cm, and a filter membrane with a pore size of 22 micrometer is installed at the outlet at the bottom of the tube to make an aluminum adsorption column;

⑥ 1.2 g gypenoside is weighed, and the amount of the b-type influenza vaccine solution is determined according to the final mass of the vaccine:the final mass of the Traditional Chinese medicinal adjuvant of 1:3, the gypenoside is prepared with double distilled water to form a solution with a concentration of 0.4 mg/ml, and then subjected to moist heat sterilization;

⑦ the aluminum adsorption column is placed vertically, the b-type influenza vaccine solution flows slowly through the aluminum adsorption column from top to bottom at a rate of 0.18 ml/min, the outlet of the tube is closed when the aluminum adsorption column is sufficiently immersed by the vaccine solution, the outlet is opened after equilibrium adsorption for 25 minutes to allow the vaccine solution to flow out, and then the gypenoside solution flows through the aluminum column in the same way for adsorption;

⑧ the adsorbed aluminum column is decant from the tube after freeze-drying, the powders with particle sizes between about 40-60 micrometers are collected to obtain the gypenoside-containing b-type influenza vaccine injection.

Example 9

A kumquat flavonoid-containing brucellosis vaccine injection is prepared in a manner of directly mixing the solutions:

① sodium chloride is weighed, and is prepared with double distilled water to form a sodium chloride solution with a concentration of 1 mol/l, and moist heat sterilization is carried out;

② 5.2 g kumquat flavonoid is weighed, and is prepared with double distilled water to form a kumquat flavonoid solution with a concentration of 1.3 mg/ml, and then moist heat sterilization is carried out;

③ a brucellosis vaccine solution and the kumquat flavonoid solution prepared in step ② are added to the sodium chloride solution prepared in step ① in a mass ratio of the brucellosis vaccine:the kumquat flavonoid of 1:7, mixed uniformly such that the volume of the final solution is 5 ml, the concentration of the brucellosis vaccine is 350 µg/ml, the concentration of kumquat flavonoid is 50 µg/ml, and the concentration of sodium chloride is 0.4 mol/l, and a mixed suspension is obtained upon standing for 15 minutes at room temperature;

④ the mixed suspension prepared in step ③ is centrifuged at 3500 times of gravitational acceleration for 30 minutes, the supernatant is discarded and the precipitate is freeze-dried, the powders with particle sizes between about 20-80 micrometers are collected to obtain the kumquat flavonoid-containing brucellosis vaccine injection.

Example 10

A rhodiola polysaccharide-containing leptospira vaccine injection is prepared by a solution dispersion-adsorption method in a manner of solidly mixing the Traditional Chinese medicinal adjuvant:

① 23 g aluminum sulfate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 100 mg of the above aluminum hydroxide adsorbed powders are resuspended in 8 ml double distilled water, and then subjected to ultrasonic processing in a ultrasonic cleaner, dispersed for 2 hours, and subjected to moist heat sterilization to give a suspension of aluminum hydroxide in water;

⑥ sodium chloride is weighed, and is prepared with double distilled water into a sodium chloride solution with a concentration of 1 mol/l, and then moist heat sterilization is carried out;

⑦ to 0.5 ml of the suspension of aluminum hydroxide in water obtained in step ⑤, a leptospira vaccine solution and the sodium chloride solution obtained in step ⑥ are added, mixed uniformly such that the volume of the final solution is 5 ml, the concentration of leptospira vaccine is 480 µg/ml, and the concentration of sodium chloride is 0.4 mol/l, and a mixed suspension is obtained upon standing for 15 minutes at room temperature;

⑧ the mixed suspension in step ⑦ is centrifuged at 3000 times of gravitational acceleration for 30 minutes, the supernatant is discarded and the precipitate is freeze-dried, the powders with particle sizes between about 30-70 micrometers are collected to obtain drug-loaded aluminium hydroxide powders of leptospira vaccine;

⑨ 6 g rhodiola polysaccharide is weighed, the rhodiola polysaccharide powders with particle sizes equivalent to those of drug-loaded aluminium hydroxide powders of leptospira vaccine, i.e., between about 30-70 micrometers, are collected, mixed uniformly with the above drug-loaded aluminium hydroxide powders of the leptospira vaccine in a mass ratio of the vaccine:the Traditional Chinese medicinal adjuvant of 1:1.25, to obtain the rhodiola polysaccharide-containing leptospira vaccine injection.

Example 11

A dioscin-containing Japanese encephalitis vaccine injection is prepared by a solution dispersion-adsorption method in a manner of liquidly mixing the Traditional Chinese medicinal adjuvant:

① 24 g aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 100 mg of the above aluminum hydroxide adsorbed powders are resuspended in 7 ml double distilled water, and then subjected to ultrasonic processing in a ultrasonic cleaner, dispersed for 2 hours, and subjected to moist heat sterilization to give a suspension of aluminum hydroxide in water;

⑥ 4.5 g dioscin is weighed, and is prepared with double distilled water to form a dioscin solution with a concentration of 0.5 mg/ml, and then moist heat sterilization is carried out;

⑦ sodium chloride is weighed, and is prepared with double distilled water to form a sodium chloride solution with a concentration of 1 mol/l, and then moist heat sterilization is carried out;

⑧ to 0.5 ml of the suspension of aluminum hydroxide in water obtained in step ⑤, a Japanese encephalitis vaccine solution and the dioscin solution obtained in step ⑥ are added in a mass ratio of the vaccine:the Traditional Chinese medicinal adjuvant of 1:1, and the sodium chloride solution obtained in step ⑦ is added, mixed uniformly such that the volume of the final solution is 5 ml, the concentration of the Japanese encephalitis vaccine is 500 µg/ml, and the concentration of sodium chloride is 0.4 mol/l, and a mixed suspension is obtained upon standing for 15 minutes at room temperature;

⑨ the mixed suspension obtained in step⑧ is centrifuged at 3500 times of gravitational acceleration for 30 minutes, and the supernatant is discarded;

⑩ the precipitate obtained in step ⑨ is freeze-dried, and the powders with particle sizes between about 30-70 micrometers are collected to obtain the dioscin-containing Japanese encephalitis vaccine injection.

Example 12

A ginseng polysaccharide-containing hepatitis A vaccine injection is prepared by an aluminum column adsorption method:

① 16 g aluminum nitrate is added into double distilled water and dissolved to prepare a saturated solution, and the insolubles are filtered off;

② an aqueous ammonia is added to the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 1.25 g of the aluminum hydroxide powders obtained in step ④ is weighed, and loaded into a cylindrical tube with a diameter of 1 cm and a length of 10 cm, and a filter membrane with a pore size of 35 micrometers is installed at the outlet at the bottom of the tube to make an aluminum adsorption column;

⑥ 1.8 g ginseng polysaccharide is weighed, and the amount of hepatitis A vaccine solution is determined according to the final mass of the vaccine:the final mass of the Traditional Chinese medicinal adjuvant of 1:3, the ginseng polysaccharide is prepared with double distilled water to form a solution with a concentration of 0.4 mg/ml, and then moist heat sterilization is carried out;

⑦ the aluminum adsorption column is placed vertically, the hepatitis A vaccine solution flows slowly through the aluminum adsorption column from top to bottom at a rate of 0.18 ml/min, the outlet of the tube is closed when the aluminum adsorption column is sufficiently immersed by the vaccine solution, the outlet is opened after equilibrium adsorption for 25 minutes to allow the vaccine solution to flow out, and then the ginseng polysaccharide solution flows through the aluminum column in the same way for adsorption;

⑧ the adsorbed aluminum column is decant from the tube after freeze-drying, the powders with particle sizes between about 40-60 micrometers are collected to obtain the ginseng polysaccharide-containing hepatitis A vaccine injection.

Example 13

A Clematis saponin-containing anthrax vaccine injection is prepared in a manner of directly mixing the solutions:

sodium chloride is weighed, and is prepared with double distilled water to form a sodium chloride solution with a concentration of 1 mol/l, and then moist heat sterilization is carried out;

② 4.9 g Clematis saponin is weighed, and is prepared with double distilled water to form a Clematis saponin solution with a concentration of 0.7 mg/ml, and then moist heat sterilization is carried out;

③ an anthrax vaccine solution and the Clematis saponin solution prepared in step ② are added to the sodium chloride solution prepared in step ① in a mass ratio of the anthrax vaccine:the Clematis saponin of 1:6.5, mixed uniformly such that the volume of the final solution is 5 ml, the concentration of the anthrax vaccine is 100 µg/ml, the concentration of the Clematis saponin is 650 µg/ml, and the concentration of the sodium chloride is 0.4 mol/l, and a mixed suspension is obtained upon standing for 15 minutes at room temperature;

④ the mixed suspension prepared in step ③ is centrifuged at 2800 times of gravitational acceleration for 30 minutes, the supernatant is discarded and the precipitate is freeze-dried, the powders with particle sizes between about 20-80 micrometers are collected to obtain the Clematis saponin-containing anthrax vaccine injection.

Example 14

A sea buckthorn flavonoid-containing plague vaccine injection is prepared by a solution dispersion-adsorption method in a manner of solidly mixing the Traditional Chinese medicinal adjuvant:

① 20 g aluminum sulfate is added into double distilled water and dissolved to prepare a saturated solution, and the insolubles are filtered off;

② an aqueous ammonia is added into the above solution dropwisely with stirring slowly until the generated white flocculent precipitate does not increase any more, allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 80 mg of the above aluminum hydroxide adsorbed powders are resuspended in 7 ml double distilled water, and then subjected to ultrasonic processing in a ultrasonic cleaner, dispersed for 2 hours, and subjected to moist heat sterilization to give a suspension of aluminum hydroxide in water;

⑥ sodium chloride is weighed, and is prepared with double distilled water to form a sodium chloride solution with a concentration of 1 mol/l, and then moist heat sterilization is carried out;

⑦ to 0.5 ml suspension of aluminum hydroxide in water obtained in step ⑤, a plague vaccine solution and the sodium chloride solution obtained in step ⑥ are added, mixed uniformly such that the volume of the final solution is 5 ml, the concentration of the plague vaccine is 510 μg/ml, and the concentration of the sodium chloride is 0.4 mol/l, and a mixed suspension is obtained upon standing for 15 minutes at room temperature;

⑧ the mixed suspension in step ⑦ is centrifuged at 3000 times of gravitational acceleration for 30 minutes, the supernatant is discarded and the precipitate is freeze-dried, the powders with particle sizes between about 30-70 micrometers are collected to obtain drug-loaded aluminium hydroxide powders of the plague vaccine;

⑨ 5 g sea buckthorn flavonoid is weighed, the sea buckthorn flavonoid powders with particle sizes equivalent to those of drug-loaded aluminium hydroxide powders of plague vaccine, i.e, between about 30-70 micrometers, are collected, mixed uniformly with the above drug-loaded aluminium hydroxide powders of the plague vaccine in a mass ratio of the vaccine:the mass of the Traditional Chinese medicinal adjuvant of 1:1.75, to obtain the sea buckthorn flavonoid-containing plague vaccine injection.

Example 15

A daidzein-containing forest encephalitis vaccine injection is prepared by a solution dispersion-adsorption method in a manner of liquidly mixing the Traditional Chinese medicinal adjuvant:

① 16 g aluminum nitrate is added into double distilled water and dissolved to prepare a saturated solution, and the insolubles are filtered off;

② an aqueous ammonia is added into the above saturated solution dropwisely with stirring slowly until the generated white flocculent precipitate does not increase any more, and then allowed to stand for 30 minutes;

③ the white flocculent precipitate generated in the above reaction is transferred into a Busher funnel, washed with double distilled water until no ammoniacal odour is left;

④ the washed precipitate is dried under vacuum, the powders with particle sizes between about 30-70 micrometers are collected to obtain aluminum hydroxide adsorbed powders;

⑤ 90 mg of the above aluminum hydroxide adsorbed powders are resuspended in 10 ml double distilled water, and then subjected to ultrasonic processing in a ultrasonic cleaner, dispersed for 2 hours, and subjected to moist heat sterilization to give a suspension of aluminum hydroxide in water;

⑥ 5.5 g daidzein is weighed, and is prepared with double distilled water to form a daidzein solution with a concentration of 0.75 mg/ml, and then moist heat sterilization is carried out;

⑦ sodium chloride is weighed, and is prepared with double distilled water to form a sodium chloride solution with a concentration of 1 mol/l, and then moist heat sterilization is carried out;

⑧ to 0.5 ml of the suspension of aluminum hydroxide in water obtained in step ⑤, a forest encephalitis vaccine solution and the daidzein solution obtained in step ⑥ are added in a mass ratio of the vaccine:the Traditional Chinese medicinal adjuvant of 1:1.2, and the sodium chloride solution obtained in step ⑦ are added, mixed uniformly such that the volume of the final solution is 5 ml, the concentration of the forest encephalitis vaccine is 560 μg/ml, and the concentration of the sodium chloride is 0.4 mol/l, and a mixed suspension is obtained upon standing for 15 minutes at room temperature;

⑨ the mixed suspension obtained in step ⑧ is centrifuged at 3500 times of gravitational acceleration for 30 minutes, and the supernatant is discarded;

⑩ the precipitate obtained in step ⑨ is freeze-dried, and the powders with particle sizes between about 30-70 micrometers are collected to obtain the daidzein-containing forest encephalitis vaccine injection.

Example 16

The tetanus toxoid vaccine injections in Table 1 are prepared in the same way as Example 1.

TABLE 1

Components of tetanus toxoid vaccine injections and the contents of the respective components

| | Content of tetanus toxoid vaccine (mg/g) | Content of Traditional Chinese medicinal adjuvant (component/mg/g) |
|---|---|---|
| Ginsenoside tetanus toxoid vaccine injection | 500 | Ginsenoside/250 |
| Ginseng polysaccharide tetanus toxoid vaccine injection | 500 | Ginseng polysaccharide/250 |
| Astragalus polysaccharide tetanus toxoid vaccine injection | 500 | Astragalus polysaccharide/250 |
| Epimedium flavonoid tetanus toxoid vaccine injection | 500 | Epimedium flavonoid/250 |

Example 17

The mumps vaccine injections in Table 2 are prepared in the same way as Example 2.

TABLE 2

Components of mumps vaccine injections and the contents of the respective components

| | Content of mumps vaccine (mg/g) | Content of aluminium adjuvant (mg/g) | Content of Traditional Chinese medicinal adjuvant (component/mg/g) |
|---|---|---|---|
| Traditional Chinese medicine negative mumps vaccine injection | 500 | 500 | — |
| Astragalus polysaccharide mumps vaccine injection | 400 | 400 | Astragalus polysaccharide/200 |

TABLE 2-continued Components of mumps vaccine injections and the contents of the respective components

| | Content of mumps vaccine (mg/g) | Content of aluminium adjuvant (mg/g) | Content of Traditional Chinese medicinal adjuvant (component/mg/g) |
|---|---|---|---|
| Ginseng polysaccharide mumps vaccine injection | 400 | 400 | Ginseng polysaccharide/200 |
| Grifola polysaccharide mumps vaccine injection | 400 | 400 | Grifola polysaccharide/200 |
| Rhodiola polysaccharide mumps vaccine injection | 400 | 400 | Rhodiola polysaccharide/200 |

Example 18

The measles vaccine injections in Table 3 are prepared in the same way as Example 3.

TABLE 3

Components of measles vaccine injections and the contents of the respective components

| | Content of measles vaccine (mg/g) | Content of aluminium adjuvant (mg/g) | Content of daidzein (mg/g) |
|---|---|---|---|
| Traditional Chinese medicine negative measles vaccine injection | 500 | 500 | — |
| Low-dose daidzein measles vaccine injection | 444 | 444 | 112 |
| Middle-dose daidzein measles vaccine injection | 400 | 400 | 200 |
| High-dose daidzein measles vaccine injection | 333 | 333 | 334 |

Example 19

The Japanese encephalitis vaccine injections in Table 4 are prepared in the same way as Example 4.

TABLE 4

Components of Japanese encephalitis vaccine injections and the contents of the respective components

| | Content of Japanese encephalitis vaccine (mg/g) | Content of aluminium adjuvant (mg/g) | Content of Traditional Chinese medicinal adjuvant (variety/mg/g) |
|---|---|---|---|
| Traditional Chinese medicine negative Japanese encephalitis vaccine injection | 366 | 634 | — |
| Ginsenoside Japanese encephalitis vaccine injection | 300 | 520 | Ginsenoside/180 |
| Notoginsenoside Japanese encephalitis vaccine injection | 300 | 520 | Notoginsenoside/180 |
| Gypenoside Japanese encephalitis vaccine injection | 300 | 520 | Gypenoside/180 |
| Dioscin Japanese encephalitis vaccine injection | 300 | 520 | Dioscin/180 |

The vaccine injections prepared in the above Examples are administered by means of needle free injection technology.

The needle free injection technology, especially needle free powder injection technology, is an administration technology that is drawing increasing concern. This technology requires the use of a needle free injector. This technology use high pressure gas to accelerate drug powders, such that the drug powders get a very high speed (e.g., 600-1000 m/s). The high-speed powders penetrate stratum corneum of the skin to reach intradermal or subcutaneous sites, so as to achieve the purpose of administration. This technology can avoid acids and enzymes to destroy the drug and breakthrough the absorbing barrier of stratum corneum, has no first-pass effect, and has a higher bioavailability. In addition, the technology is easy to use and avoid the sense of fear of a patient to needle injection.

The specific operations are as follows:

(1) the powder vaccine injections prepared in the above Examples are loaded into a kit of a needle free injector;

(2) carry out needle free injection.

The following is provided to illustrate the characteristics of the prevention and treatment of different diseases, and different doses of vaccine injections are used for immunization to achieve optimal prevention and treatment effects.

1. For the prevention and treatment of pertussis: using the notoginsenoside-containing pertussis vaccine injection, 45-75 micrograms per injection, performing booster inoculation once after two weeks;

2. For the prevention and treatment of tetanus: using the ginsenoside-containing tetanus toxoid vaccine injection, 20-30 micrograms per injection, performing booster inoculation once after two weeks;

3. For the prevention and treatment of mumps: using the *astragalus* polysaccharide-containing mumps vaccine injection, 40-60 micrograms per injection, performing booster inoculation once after three weeks;

4. For the prevention and treatment of diphtheria: using the epimedium flavonoid-containing diphtheria vaccine injection, 15-25 micrograms per injection, performing booster inoculation once after two weeks;

5. For the prevention and treatment of measles: using the grifola polysaccharide-containing measles vaccine injection, 35-50 micrograms per injection, performing booster inoculation once after three weeks;

6. For the prevention and treatment of rubella: using the *Hedyotis diffusa* flavonoid-containing rubella vaccine injection, 45-60 micrograms per injection, performing booster inoculation once after three weeks;

7. For the prevention and treatment of typhoid: using the jujube polysaccharide-containing typhoid vaccine injection, 25-40 micrograms per injection, performing booster inoculation once every two weeks, inoculation for three time in total;

8. For the prevention and treatment of b-type influenza: using the gypenoside-containing b-type influenza vaccine injection, 25-50 micrograms per injection;

9. For the prevention and treatment of brucellosis: using the kumquat flavonoid-containing brucellosis vaccine injection, 30-60 micrograms per injection;

10. For the prevention and treatment of leptospirosis: using the rhodiola polysaccharide-containing leptospira vaccine injection, 40-65 micrograms per injection, performing booster inoculation once after one week;

11. For the prevention and treatment of Japanese encephalitis: using the dioscin-containing Japanese encephalitis vaccine injection, 15-30 micrograms per injection;

12. For the prevention and treatment of hepatitis A: using the ginseng polysaccharide-containing hepatitis A vaccine injection, 10-25 micrograms per injection;

13. For the prevention and treatment of anthrax: using the Clematis saponin-containing anthrax vaccine injection, 25-45 micrograms per injection;

14. For the prevention and treatment of plague: using the sea buckthorn flavonoid-containing plague vaccine injection, 35-55 micrograms per injection;

15. For the prevention and treatment of forest encephalitis: using the daidzein-containing forest encephalitis vaccine injection, 30-50 micrograms per injection, performing booster inoculation once after two weeks;

The following experimental results show the obvious advantages of the needle free powder injection of the vaccine injections in Examples 1-19:

(1) Investigation on Immune Effect of Tetanus Toxoid Vaccine Injections Containing Different Traditional Chinese Medicinal Adjuvants Detection for in vivo immunogenicity is carried out for the vaccine injection obtained in Example 16 in guinea pigs. The guinea pigs to be used are male Dunkin Hartley guinea pigs. 36 guinea pigs are randomly divided into 6 groups in accordance with Table 5: blank group, negative control group of Traditional Chinese medicine, ginsenoside group, ginseng polysaccharide group, *astragalus* polysaccharide group, and epimedium flavonoid group with 6 in each group. Wherein: physiologic saline is injected into each animal in the blank group conventionally with a dose of 4 mg per kg of body weight, tetanus toxoid vaccine is injected into each animal in the negative control group of Traditional Chinese medicine conventionally with a dose of 4 mg tetanus toxoid vaccine per kg of body weight, ginsenoside-containing tetanus toxoid vaccine injection prepared in Example 16 is injected into each animal in the ginsenoside group by a needle free powder injector according to a dose of 4 mg tetanus toxoid vaccine per kg of body weight, the ginseng polysaccharide-containing tetanus toxoid vaccine injection prepared in Example 16 is injected into each animal in the ginseng polysaccharide group by a needle free powder injector according to a dose of 4 mg tetanus toxoid vaccine per kg of body weight, the *astragalus* polysaccharide-containing tetanus toxoid vaccine injection prepared in Example 16 is injected into each animal in the *astragalus* polysaccharide group by a needle free powder injector according to a dose of 4 mg tetanus toxoid vaccine per kg of body weight, and the epimedium flavonoid-containing tetanus toxoid vaccine injection prepared in Example 16 is injected into each animal in the epimedium flavonoid group by a needle free powder injector according to a dose of 4 mg tetanus vaccine per kg of body weight. On day 63 after injection, the concentration of the tetanus toxoid antibody IgG in serum of the guinea pigs is detected. The concentration of the antibody is detected using an ELISA tetanus kit (Zhuhai Haiqin biopharmaceutical co., LTD) in a manner provided by the manufacturer. See Table 5 for the result.

Use t-test to carry out statistical analysis for the result, the concentration of the tetanus toxoid antibody is represented as mean±standard deviation, *$p<0.1$ vs Traditional Chinese medicine negative control; **$p<0.05$ vs Traditional Chinese medicine negative control (n=6).

TABLE 5

Detection result of immunogenicity for the tetanus toxoid vaccine injections

| | Dose of tetanus toxoid vaccine (mg/kg of body weight) | Content of Traditional Chinese medicinal adjuvant (mg/kg of body weight) | Concentration of tetanus toxoid antibody after 63 days (IU/ml) |
|---|---|---|---|
| Blank group | 0 | 0 | — |
| Negative control group of Traditional Chinese medicine | 4 | 0 | 1.42 ± 0.35 |
| Ginsenoside group | 4 | 2 | 2.01 ± 0.51* |
| Ginseng polysaccharide group | 4 | 2 | 2.11 ± 0.46* |

TABLE 5-continued Detection result of immunogenicity for the tetanus toxoid vaccine injections

|  | Dose of tetanus toxoid vaccine (mg/kg of body weight) | Content of Traditional Chinese medicinal adjuvant (mg/kg of body weight) | Concentration of tetanus toxoid antibody after 63 days (IU/ml) |
|---|---|---|---|
| Astragalus polysaccharide group | 4 | 2 | 2.23 ± 0.61* |
| Epimedium flavonoid group | 4 | 2 | 2.04 ± 0.53* |

(2) Investigation on Immune Effect of Mumps Vaccine Injections Containing Different Traditional Chinese Medicinal Adjuvants Detection for in vivo immunogenicity is carried out for the vaccine injections obtained in Example 17 in rats. The rats to be used are male Wistar rats. 36 rats are randomly divided into 6 groups in accordance with Table 6: blank group, negative control group of Traditional Chinese medicine, *astragalus* polysaccharide group, ginseng polysaccharide group, grifola polysaccharide group, and rhodiola polysaccharide group with 6 in each group. Wherein: physiologic saline is injected into each animal in the blank group conventionally according to a dose of 6 mg per kg of body weight, mumps vaccine is injected into each animal in the negative control group of Traditional Chinese medicine conventionally according to a dose of 6 mg mumps vaccine per kg of body weight, the *astragalus* polysaccharide-containing mumps vaccine injection prepared in Example 17 is injected into each animal in the *astragalus* polysaccharide group by a needle free powder injector according to a dose of 6 mg mumps vaccine per kg of body weight, the ginseng polysaccharide-containing mumps vaccine injection prepared in Example 17 is injected into each animal in the ginseng polysaccharide group by a needle free powder injector according to a dose of 6 mg mumps vaccine per kg of body weight, the grifola polysaccharide-containing mumps vaccine injection prepared in Example 17 is injected into each animal in the grifola polysaccharide group by a needle free powder injector according to a dose of 6 mg mumps vaccine per kg of body weight, and the rhodiola polysaccharide-containing mumps vaccine injection prepared in Example 17 is injected into each animal in the rhodiola polysaccharide group by a needle free powder injector according to a dose of 6 mg mumps vaccine per kg of body weight. On Day 112 after injection, the concentration of the mumps antibody IgM in serum of the rats is detected. The concentration of the antibody is detected using an ELISA mumps detection kit (Shenzhen Anqun bioengineering co., LTD) in a manner provided by the manufacturer. See Table 6 for the result.

Use t-test to carry out statistical analysis for the result, the concentration of the mumps antibody is represented as mean±standard deviation, *p<0.1 vs Traditional Chinese medicine negative control; **p<0.05 vs Traditional Chinese medicine negative control (n=6).

TABLE 6

Detection result of immunogenicity for the mumps vaccine injections

|  | Dose of vaccine injection (mg/kg of body weight) | Content of Traditional Chinese medicinal adjuvant (mg/kg of body weight) | Concentration of mumps antibody after 112 days (IU/ml) |
|---|---|---|---|
| Blank group | 0 | 0 | — |
| Negative control group of Traditional Chinese medicine | 6 | 0 | 3.15 ± 0.74 |
| Astragalus polysaccharide group | 6 | 3 | 4.46 ± 1.12* |
| Ginseng polysaccharide group | 6 | 3 | 4.23 ± 0.89* |
| Grifola polysaccharide group | 6 | 3 | 5.42 ± 1.48** |
| Rhodiola polysaccharide group | 6 | 3 | 5.10 ± 1.97* |

(3) Investigation on Immune Effect of Measles Vaccine Injections Containing Different Concentrations of Daidzein Detection for in vivo immunogenicity is carried out for the vaccine injections obtained in Example 18 in guinea pigs. The guinea pigs to be used are male Dunkin Hartley guinea pigs. 30 rats are randomly divided into 5 groups in accordance with Table 7: blank group, negative control group of Traditional Chinese medicine, low dose group of daidzein group, middle dose group of daidzein group, and high dose group of daidzein group with 6 in each group. Wherein: physiologic saline is injected into each animal in the blank group conventionally according to a dose of 5 mg per kg of body weight, measles vaccine is injected into each animal in the negative control group of Traditional Chinese medicine conventionally according to a dose of 5 mg measles vaccine per kg of body weight, low-dose daidzein measles vaccine injection prepared in Example 18 is injected into each animal in the low dose group of daidzein group by a needle free powder injector according to a dose of 5 mg measles vaccine per kg of body weight, middle-dose daidzein measle needle free powder vaccine injection prepared in Example 18 is injected into each animal in the middle dose group of daidzein group by a needle free powder injector according to a dose of 5 mg measles vaccine per kg of body weight, and high-dose daidzein measles vaccine injection prepared in Example 18 is injected into each animal in the high dose group of daidzein group by a needle free powder injector according to a dose of 5 mg measles vaccine per kg of body weight. On Day 56 after injection, the concentration of the measle antibody IgM in serum of the guinea pigs is detected. The concentration of the antibody is detected using an ELISA measle detection kit (Shanghai Zhonghua biological technology co., LTD) in a manner provided by the manufacturer. See Table 7 for the result.

Use t-test to carry out statistical analysis for the result, the concentration of the measle antibody is represented as mean±standard deviation, *p<0.1 vs Traditional Chinese medicine negative control; **p<0.05 vs Traditional Chinese medicine negative control (n=6).

TABLE 7

Detection result of immunogenicity for the measles vaccine injections

| | Dose of vaccine injection (mg/kg of body weight) | Content of Traditional Chinese medicinal adjuvant (mg/kg of body weight) | Concentration of measle antibody after 56 days (IU/ml) |
|---|---|---|---|
| Blank group | 0 | 0 | — |
| Negative control group of Traditional Chinese medicine | 5 | 0 | 3.88 ± 1.42 |
| Low dose group of daidzein group | 5 | 1.25 | 6.05 ± 1.87* |
| Middle dose group of daidzein group | 5 | 2.5 | 6.65 ± 2.32* |
| High dose group of daidzein group | 5 | 5 | 8.94 ± 2.58* |

(4) Investigation on Immune Effect of Japanese Encephalitis Vaccine Injections Containing Different Traditional Chinese Medicinal Adjuvants Detection for in vivo immunogenicity is carried out for the vaccine injections obtained in Example 19 in guinea pigs. The guinea pigs to be used are male Dunkin Hartley guinea pigs. 36 rats are randomly divided into 6 groups in accordance with Table 8: blank group, negative control group of Traditional Chinese medicine, ginsenoside group, notoginsenoside group, gypenoside group, and dioscin group with 6 in each group. Wherein: physiologic saline is injected into each animal in the blank group conventionally according to a dose of 3 mg per kg of body weight, Japanese encephalitis vaccine is injected into each animal in the negative control group of Traditional Chinese medicine conventionally according to a dose of 3 mg Japanese encephalitis vaccine per kg of body weight, the ginsenoside-containing Japanese encephalitis vaccine injection prepared in Example 19 is injected into each animal in the ginsenoside group by a needle free powder injector according to a dose of 3 mg Japanese encephalitis vaccine per kg of body weight, the notoginsenoside-containing Japanese encephalitis vaccine injection prepared in Example 19 is injected into each animal in the notoginsenoside group with a needle free powder injector according to a dose of 3 mg Japanese encephalitis vaccine per kg of body weight, the gypenoside-containing Japanese encephalitis vaccine injection prepared in Example 19 is injected into each animal in the gypenoside group by a needle free powder injector according to a dose of 3 mg Japanese encephalitis vaccine per kg of body weight, and the dioscin-containing Japanese encephalitis vaccine injection prepared in Example 19 is injected into each animal in the dioscin group by a needle free powder injector according to a dose of 3 mg Japanese encephalitis vaccine per kg of body weight. On Day 84 after injection, the concentration of the Japanese encephalitis antibody IgM in serum of the guinea pigs is detected. The concentration of the antibody is detected using a Japanese encephalitis kit (Shanghai Yueyan biological technology co., LTD) in a manner provided by the manufacturer. See Table 8 for the result.

Use t-test to carry out statistical analysis for the result, the concentration of the Japanese encephalitis antibody is represented as mean±standard deviation, *p<0.1 vs Traditional Chinese medicine negative control; **p<0.05 vs Traditional Chinese medicine negative control (n=6).

TABLE 8

Detection result of immunogenicity for the Japanese encephalitis vaccine injections

| | Dose of vaccine injection (mg/kg of body weight) | Content of Traditional Chinese medicinal adjuvant (mg/kg of body weight) | Concentration of Japanese encephalitis antibody after 84 days (IU/ml) |
|---|---|---|---|
| Blank group | 0 | 0 | — |
| Negative control group of Traditional Chinese medicine | 3 | 0 | 6.16 ± 1.90 |
| Ginsenoside group | 3 | 1.8 | 9.33 ± 2.42* |
| Notoginsenoside group | 3 | 1.8 | 9.14 ± 2.38* |
| Gypenoside group | 3 | 1.8 | 9.82 ± 1.75** |
| Dioscin group | 3 | 1.8 | 8.94 ± 2.07* |

As can be seen, after the guinea pigs is immunized by administering the Traditional Chinese medicinal adjuvant-containing vaccine injection of the present invention, the concentration of the antibody generated by the guinea pigs is higher, which proves that the Traditional Chinese medicinal adjuvants have an activity of enhancing the immunization. Although the immune enhancement effects are different among different kinds of Traditional Chinese medicinal ingredients, in general, enhancement effect of the Traditional Chinese medicine adjuvants for the powder vaccines is very significant.

It has been proved in practice that, the vaccine injection of the present invention, as a new formulation for immunization, is easy to use, has low dosage, onset rapidly, has both the advantages of vaccine and Traditional Chinese medicinal adjuvant, has a synergistic effect, and thus has a good market prospect.

INDUSTRIAL APPLICABILITY

The vaccine injection of the present invention has both the advantages of aluminium adjuvant and Traditional Chinese medicinal adjuvant. Aluminum hydroxide particles as an aluminium adjuvant have a high surface energy, and are capable of generating adsorption for substances such as a protein, so that the vaccine is combined to the surface of the aluminum hydroxide particles and they finally form a stable powder system together. Moreover, aluminum hydroxide itself, in addition to acting as an immunologic adjuvant, also possesses flocculent adsorption function, and a substrate of solid vaccine developed on the basis of the adsorption function can give full play to the pharmaceutic advantage thereof. The Traditional Chinese medicinal adjuvant has certain absorption and loading ability, which can assist in solidification, and thus makes up for the lack of absorption capacity of the aluminum adjuvant. Furthermore, the immune response caused by a Traditional Chinese medicinal adjuvant is more complex, which can induce both humoral immunity and cell immunity. On the other hand, since the Traditional Chinese medicinal adjuvant reaching the administration site is solid powder microparticles, and the microparticles themselves are intensely immunogenic, the pre-stimulation generated on immune system is more intense; at the same time, since the diffusion rate of the solid formulation via the body fluid in vivo is low, and it is not easy for the aluminium element in a composite adjuvant to enter into the fluid circulation, the vaccine injection not only reduces the side effect of the aluminum adjuvant, but also has some slow-release effect.

The vaccine injection of the present invention provides a new formulation of vaccine, which is especially suitable for needle free injection technology, and thus effectively avoids the first pass effect due to oral pharmaceutical preparation. The particle size of the vaccine injection is in conformity with the requirement for percutaneous administration, easy to pass the stratum corneum barrier, and can significantly improve drug efficacy and shorten the onset time. Therefore, the vaccine injection adapted for needle free injection technology is especially suitable for medical prevention guarantee in the condition of serious emergencies and remote areas, large-scale field operations and the like, and a patient who fears needle (e.g., a children) and a patient who requires long-term self-administration, and thus has a very broad application prospect.

The present invention adopts direct solution mixing method, solution dispersion-adsorption method or aluminum adsorption column methods to prepare a powder injection vaccine. The direct solution mixing method and solution dispersion-adsorption method are convenient, the procedures are short, and the cost is low; while the aluminum adsorption column method is suitable for the preparation of powders in large-scale.

What we claim is:

1. A vaccine injection consisting of a vaccine, a Traditional Chinese medicinal adjuvant and an aluminum adjuvant in a mass ratio of 1:0.5:0.8-1:10:20, wherein the vaccine injection is in a form of a powder and the size of the powder is between 10-120 micrometers, wherein said vaccine is mumps vaccine, said Chinese medicinal adjuvant is *astragalus* polysaccharide, and wherein said vaccine injection is obtained by the following preparation steps:

preparing an aluminum adsorption column with aluminum hydroxide as a supporter, flowing a solution of said vaccine and a solution of said Traditional Chinese medicinal adjuvant through said aluminum adsorption column, drying said aluminum adsorption column, and collecting powders with particle sizes between 10-120 micrometers, to obtain the vaccine injection.

2. The vaccine injection of claim 1 wherein the vaccine injection is suitable for administration by needle-free injection.

3. The vaccine injection of claim 1, wherein the step of flowing the solution of the vaccine and the solution of the Traditional Chinese medicinal adjuvant through the aluminum adsorption column comprises: flowing the solution of the vaccine through the aluminum adsorption column, and then flowing the solution of the Traditional Chinese medicinal adjuvant through the aluminum adsorption column.

4. The vaccine injection of claim 1, wherein the step of flowing the solution of the vaccine and the solution of the Traditional Chinese medicinal adjuvant through the aluminum adsorption column comprises: flowing the solution of the Traditional Chinese medicinal adjuvant through the aluminum adsorption column, and then flowing the solution of the vaccine through the aluminum adsorption column.

5. The vaccine injection of claim 1, wherein the step of flowing the solution of the vaccine and the solution of the Traditional Chinese medicinal adjuvant through the aluminum adsorption column comprises: mixing the solution of vaccine and the solution of the Traditional Chinese medicinal adjuvant together, and then flowing the mixed solution through the aluminum adsorption column.

6. The vaccine injection of claim 1, wherein said vaccine, said Traditional Chinese medicinal adjuvant and said aluminum adjuvant are present in a mass ratio of 1:1:5-1:1:10.

7. The vaccine injection of claim 1, wherein the size of the powder is between 30-70 micrometers.

8. The vaccine injection of claim 6, wherein the size of the powder is between 30-70 micrometers.

* * * * *